(12) United States Patent
Boyd et al.

(10) Patent No.: US 9,033,933 B2
(45) Date of Patent: May 19, 2015

(54) MEDICATED MODULE WITH LOCKABLE NEEDLE GUARD

(75) Inventors: Malcolm Stanley Boyd, Wellsbourne (GB); James Alexander Davies, Leamington Spa (GB); Daniel Thomas De Sausmarez Lintell, Rugby (GB)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 394 days.

(21) Appl. No.: 13/576,633

(22) PCT Filed: Feb. 1, 2011

(86) PCT No.: PCT/EP2011/051405
§ 371 (c)(1),
(2), (4) Date: Dec. 17, 2012

(87) PCT Pub. No.: WO2011/095486
PCT Pub. Date: Aug. 11, 2011

(65) Prior Publication Data
US 2013/0110050 A1 May 2, 2013

Related U.S. Application Data

(60) Provisional application No. 61/301,708, filed on Feb. 5, 2010.

(30) Foreign Application Priority Data

Apr. 23, 2010 (EP) .................................. 10160845.3

(51) Int. Cl.
*A61M 5/32* (2006.01)
*A61M 5/24* (2006.01)
*A61M 5/31* (2006.01)

(52) U.S. Cl.
CPC ............... *A61M 5/3294* (2013.01); *A61M 5/24* (2013.01); *A61M 5/2448* (2013.01); *A61M 5/3146* (2013.01); *A61M 5/3257* (2013.01)

(58) Field of Classification Search
CPC ............ A61M 5/3257; A61M 5/3294; A61M 5/2448; A61M 5/3146
USPC .................. 604/110, 191–192, 198, 200–201, 604/205–207, 212, 214, 232
See application file for complete search history.

(56) References Cited

U.S. PATENT DOCUMENTS 4,822,340 A * 4/1989 Kamstra ....................... 604/135
5,242,401 A 9/1993 Colsky
(Continued)

FOREIGN PATENT DOCUMENTS

| EP | 0350186 | 1/1990 |
|---|---|---|
| JP | H02-104369 | 4/1990 |
| JP | H10-502829 | 3/1998 |
| WO | 95/28201 | 10/1995 |
| WO | 2007/026163 | 3/2007 |
| WO | 2008/114035 | 9/2008 |

OTHER PUBLICATIONS

International Search Report and Written Opinion for Int. App. No. PCT/EP2011/051405, mailed May 11, 2011.
(Continued)

*Primary Examiner* — Theodore Stigell
*Assistant Examiner* — Amber Stiles
(74) *Attorney, Agent, or Firm* — McDonnell Boehnen Hulbert & Berghoff LLP

(57) ABSTRACT

A medicated module for an injection system to co-deliver at least two medicaments is disclosed where a primary delivery device containing a primary medicament accepts a medicated module containing a single dose of a secondary medicament and where both medicaments are delivered through a single hollow needle. The medicated module is configured so that it will first deliver both the primary and secondary medicaments and then, if needed, a dose(s) of additional primary medicament. The module also contains a needle guard that locks the first dose delivery, but can be manually overridden by a user to perform a second or subsequent injection of primary medicament.

14 Claims, 4 Drawing Sheets

(56) References Cited

U.S. PATENT DOCUMENTS

| | | | |
|---|---|---|---|
| 5,281,198 | A | 1/1994 | Haber et al. |
| 6,562,002 | B1 | 5/2003 | Taylor |
| 2002/0068909 | A1* | 6/2002 | Alchas et al. ............... 604/198 |
| 2003/0120209 | A1 | 6/2003 | Jensen et al. |
| 2006/0229562 | A1 | 10/2006 | Marsh et al. |
| 2006/0276755 | A1 | 12/2006 | Sullivan et al. |
| 2007/0100288 | A1 | 5/2007 | Bozeman et al. |
| 2008/0215001 | A1* | 9/2008 | Cowe ............................ 604/110 |
| 2009/0018506 | A1* | 1/2009 | Daily et al. .................. 604/136 |

OTHER PUBLICATIONS

First Office Action issued for corresponding Chinese Patent App. No. 201180017650.1, issued Nov. 25, 2013.

International Preliminary Report on Patentability for Int. App. No. PCT/EP2011/051405, mailed Aug. 16, 2012.

Chinese Office Action for CN App. No. 201180017650.1, dated Aug. 27, 2014.

Japanese Office Action for JP App. No. 2012-551598, mailed Sep. 24, 2014.

* cited by examiner

MEDICATED MODULE WITH LOCKABLE NEEDLE GUARD

CROSS REFERENCE TO RELATED APPLICATIONS

The present application is a U.S. National Phase Application pursuant to 35 U.S.C. §371 of International Application No. PCT/EP2011/051405 filed Feb. 1, 2011, which claims priority to U.S. Provisional Patent Application No. 61/301,708 filed on Feb. 5, 2010 and European Patent Application No. 10160845.3 filed Apr. 23, 2010. The entire disclosure contents of these applications are herewith incorporated by reference into the present application.

FIELD OF INVENTION

Specific embodiment of this disclosure relate to medical devices and methods of delivering at least two drug agents from separate reservoirs using devices having only a single dose setting mechanism and a single dispense interface. A single delivery procedure initiated by the user may cause a non-user settable dose of a second drug agent and a variable set dose of a first drug agent to be delivered to the patient. The drug agents may be available in two or more reservoirs, containers or packages, each containing independent (single drug compound) or pre-mixed (co-formulated multiple drug compounds) drug agents. Specifically, our disclosure concerns a medicated module where after a first dose delivery the user has the option to consciously unlock the module to perform a second dose delivery of the first drug agent. This may be of particular benefit where the therapeutic response can be optimized for a specific target patient group, through control and definition of the therapeutic profile.

BACKGROUND

Certain disease states require treatment using one or more different medicaments. Some drug compounds need to be delivered in a specific relationship with each other in order to deliver the optimum therapeutic dose. Here, combination therapy may be desirable, but not possible in a single formulation for reasons such as, but not limited to, stability, compromised therapeutic performance and toxicology.

For example, in some cases it might be beneficial to treat a diabetic with a long acting insulin and with a glucagon-like peptide-1 (GLP-1), which is derived from the transcription product of the proglucagon gene. GLP-1 is found in the body and is secreted by the intestinal L cell as a gut hormone. GLP-1 possesses several physiological properties that make it (and its analogs) a subject of intensive investigation as a potential treatment of diabetes mellitus.

There are a number of potential problems when delivering two active medicaments or "agents" simultaneously. The two active agents may interact with each other during the long-term, shelf life storage of the formulation. Therefore, it is advantageous to store the active components separately and only combine them at the point of delivery, e.g. injection, needle-less injection, pumps, or inhalation. However, the process for combining the two agents needs to be simple and convenient for the user to perform reliably, repeatedly and safely.

A further problem is that the quantities and/or proportions of each active agent making up the combination therapy may need to be varied for each user or at different stages of their therapy. For example one or more actives may require a titration period to gradually introduce a patient up to a "maintenance" dose. A further example would be if one active requires a non-adjustable fixed dose while the other is varied in response to a patient's symptoms or physical condition. This problem means that pre-mixed formulations of multiple active agents may not be suitable as these pre-mixed formulations would have a fixed ratio of all the active components, which could not be varied by the healthcare professional or user.

Additional problems arise where a multi-drug compound therapy is required, because many users cannot cope with having to use more than one drug delivery system or make the necessary accurate calculation of the required dose combination. This is especially true for users with dexterity or cognitive difficulties. In some circumstances it is also necessary to perform a priming procedure of the device and/or needle cannulae before dispensing the medicaments. Likewise, in some situations, it may be necessary to bypass one drug compound and to dispense only a single medicament from a separate reservoir.

Accordingly, there exists a strong need to provide devices and methods for the delivery of two or more medicaments in a single injection or delivery step that is simple for the user to perform. Specific embodiments of the disclosed medicated module and drug delivery device overcome the above-mentioned problems by providing separate storage containers for two or more active drug agents that are then only combined and/or delivered to the patient during a single delivery procedure. Setting a dose of one medicament automatically fixes or determines the dose of the second medicament (i.e. non-user settable). Here, also the opportunity may be provided to vary the quantity of one or both medicaments. For example, one fluid quantity can be varied by changing the properties of the injection device (e.g. dialing a user variable dose or changing the device's "fixed" dose). The second fluid quantity can be changed by manufacturing a variety of secondary drug containing packages with each variant containing a different volume and/or concentration of the second active agent. The user or healthcare professional would then select the most appropriate secondary package or series or combination of series of different packages for a particular treatment regime.

This disclosure provides a medicated module that allows the user to consciously choose to perform more than one injection using the same needle. This may be accomplished by configuring the medicated module with a button or other release mechanism that the user can activate to unlock a needle guard to allow for a second injection of primary medicament once the combination of primary and secondary medicament has been injected.

These and other advantages will become evident from the following more detailed description of the invention.

One problem to be solved by the present invention is to provide a medicated module and a drug delivery system where the administration of a medicament is improved.

SUMMARY

Specific embodiments of the disclosed medicated module and drug delivery device allow complex combinations of multiple drug compounds within a single drug delivery system. In particular, a user may set and dispense a multi-drug compound device though one single dose setting mechanism and a single dispense interface. This single dose setter may control the mechanism of the device such that a predefined combination of the individual drug compounds is delivered when a single dose of one of the medicaments is set and dispensed through the single dispense interface. The term drug dispense interface may be, in the context of this disclosure, any type of outlet that allows the two or more medicaments to exit the drug delivery system and be delivered to the patient. In a preferred embodiment the single drug dispense interface comprises a hollow needle cannula.

By defining the therapeutic relationship between the individual drug compounds our delivery device may help ensure that a patient/user receives the optimum therapeutic combination dose from a multi-drug compound device without the inherent risks associated with multiple inputs where the user has to calculate and set the correct dose combination every time they use the device. The medicaments can be fluids, defined herein as liquids or gases or powders that are capable of flowing and that change shape at a steady rate when acted upon by a force tending to change its shape. Alternatively, one of the medicaments may be a solid that is carried, solubilized or otherwise dispensed with another fluid medicament.

The disclosed medicated module and drug delivery device may be of particular benefit to users with dexterity or cognitive difficulties as the single input and associated predefined therapeutic profile removes the need for them to calculate their prescribed dose every time they use the device and the single input allows considerably easier setting and dispensing of the combined compounds.

In a preferred embodiment a master drug compound, such as insulin, contained within a multiple dose, user selectable device could be used with a single use, user replaceable, module that contains a single dose of a secondary medicament and the single dispense interface. When connected to the primary device the secondary compound is activated/delivered on dispense of the primary compound. Although, in this disclosure, specifically insulin is mentioned, insulin analogs or insulin derivatives, and GLP-1 or GLP-1 analogs as two possible drug combinations, other drugs or drug combinations, such as an analgesics, hormones, beta agonists or corticosteroids, or a combination of any of the above-mentioned drugs could be used.

In the following, the term "insulin" shall mean insulin, insulin analogs, insulin derivatives or mixtures thereof, including human insulin or a human insulin analogs or derivatives. Examples of insulin analogs are, without limitation, Gly(A21), Arg(B31), Arg(B32) human insulin; Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala (B26) human insulin; Des(B28-B30) human insulin; Des (B27) human insulin or Des(B30) human insulin. Examples of insulin derivatives are, without limitation, B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

As used herein the term "GLP-1" shall mean GLP-1, GLP-1 analogs, or mixtures thereof, including without limitation, exenatide (Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH$_2$), Exendin-3, Liraglutide, or AVE0010 (H-His-Gly-Glu-Gly-Thr-Phe-Thr-Ser-Asp-Leu-Ser-Lys-Gln-Met-Glu-Glu-Ala-Val-Arg-Leu-Phe-Ile-Glu-Trp-Leu-Lys-Asn-Gly-Gly-Pro-Ser-Ser-Gly-Ala-Pro-Pro-Ser-Lys-Lys-Lys-Lys-Lys-Lys-NH$_2$).

Examples of beta agonists are, without limitation, salbutamol, levosalbutamol, terbutaline, pirbuterol, procaterol, metaproterenol, fenoterol, bitolterol mesylate, salmeterol, formoterol, bambuterol, clenbuterol, indacaterol.

Hormones are for example hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

In one aspect, there is provided a medicated module attachable to a drug delivery device. The medicated module may comprise a housing having a proximal end and a distal end, where the proximal end may have a connector configured for attachment to a drug delivery device. The medicated module may comprise a reservoir for retaining a medicament. In a preferred embodiment, the drug delivery device comprises a primary reservoir of a first medicament and the medicated module comprises a secondary reservoir comprising a second medicament. In particular, the reservoir of the medicated module may be filled by the second medicament before it is attached to the drug delivery device. The drug delivery device, in particular the primary reservoir, is preferably filled with first medicament before the module is attached to the device. The drug delivery device may be an injection device, and, in particular, a pen-type injection device. The device may be suitable to set and dispense a dose of the first medicament before the medicated module is attached to the device or after the medicated module was removed from the device. Accordingly, the device may be suitable to form a stand-alone device, configured to operate also in absence of the medicated module, for example. For this purpose, a needle cannula may be, preferably removably, attachable to the distal end of the device.

The reservoir of the medicated module may be positioned in a portion of the housing that contains a dose, for example a single dose, of a medicament. As examples, the medicament in the reservoir may comprise a GLP-1 or may comprise a premix of insulin and a GLP-1. The medicated module may comprise a cavity. The cavity may contain the reservoir. The cavity may contain and a first and a second needle cannula. The first and second needle cannulae may be configured to allow fluid communication with the reservoir.

The medicated module may be a medicated needle. The medicated module may comprise a first or proximal needle cannula. The medicated module may comprise a second or distal needle cannula. The reservoir of the medicated module may be arranged in the axial direction between the first and the second needle cannula. The needle cannulae may be configured for establishing fluid communication with the reservoir of the medicated module. The distal end of the second needle cannula may be configured for being applied to an injection site. The proximal end of the second needle cannula may be configured for piercing the reservoir of the module, in particular a seal or septum arranged at the distal end of the reservoir. The distal end of the first needle cannula may be configured for piercing the reservoir of the module, in particular a seal or septum arranged at the proximal end of the reservoir. The proximal end of the first needle cannula may be configured for piercing the primary reservoir, in particular a seal or septum arranged at the distal end of the primary reservoir of the drug delivery device.

The medicated module may comprise a needle guard to provide protection against at least one needle cannula, which may be arranged in a portion of the medicated module. The needle guard may be configured to move in an axial direction, for example a proximal direction, during application to an injection site. The needle guard may be operably connected to the housing. A release mechanism, for example a button, pip, knob or other release mechanism, may be accessible by a user to consciously unlock a guard lock. The guard lock may prevent the needle guard from moving axially after dispensing the medicament from the reservoir of the medicated module. Preferably, the guard lock may lock the needle guard, when the needle guard has returned to an extended position, covering the injection needle. The guard lock may be activated when the needle guard is first applied to an injection site and retracted into the housing. The guard lock may prevent any further use of an injection needle that may be mounted in an inner housing, unless the user consciously unlocks the module to allow for a subsequent injection using the same needle. An activation of the release mechanism may unlock the guard lock to allow one or more additional retractions of the needle guard after dispensing the medicament. After each retraction the guard lock may at least temporarily lock the needle guard from axial movement. The unlock/release mechanism and, in particular, an unlock/release button can have one or more tactile features accessible to a user to move the button to unlock the guard lock to allow a second application to an injection site. After a predefined number of retractions of the needle guard, the needle guard may be permanently locked from axial movement such that unlocking is disabled.

The guard lock may comprise a rotating sleeve operably connected to the needle guard. Such a design may allow the release mechanism, for example a button, to engage the sleeve to cause it to rotate from a second locked position to a third unlocked position. The first position of the sleeve is the starting position prior to use where the needle guard is also unlocked. The second position is a locked position after the first retraction (injection) and consequent extension of the needle guard and the fourth position is again a locked position after a second retraction and extension of the needle guard. In further embodiments, a guard lock may have a design different from a rotating sleeve. Moreover, a guard lock may have more or less than two positions, where the needle guard is unlocked, and more or less than two positions where the needle guard is locked.

The first needle cannula may be mounted in the medicated module, for example in a proximal end of the housing. The first needle cannula may be configured to provide fluid communication with the primary medicament in a drug delivery device when the medicated module is connected thereto. The medicated module may further comprise the second needle cannula. The second needle cannula may be mounted in an inner housing inside a housing of the medicated module. The reservoir of the medicated module, preferably containing a sealed capsule, may define a cavity. The cavity may be defined by a portion of a housing and a portion of an inner housing of the medicated module. The cavity may have a top volume, which may be defined by a portion of a housing, and a bottom volume, which may be defined by a portion of an inner housing. The first and second needle cannulae may be in fluid communication with the cavity. Moreover, a fluid path may be defined in the cavity bypassing the reservoir. Thereby, a priming operation may be enabled.

In one embodiment, the reservoir contains a movable bung dividing the reservoir into a distal volume and a proximal volume, and more preferably the bung separates a medicament in the proximal volume from a medicament in the distal volume. In particular, the proximal volume may contain a single dose of medicament and the distal volume may contain a fixed amount of primary medicament. In this embodiment, during a priming operation prior to a dose delivery operation the bung may move in a distal direction, thereby expelling medicament from the distal volume. After movement of the bung, the medicament in the proximal volume may be dispensable around the bung. In particular, priming may be accomplished by moving the bung into a distal direction by setting a small dose of primary medicament using the drug delivery device equal to the volume of primary medicament contained in the distal volume of the cavity. Upon activation of the dose button on the device, the primary medicament may flow from the primary reservoir in the device into the proximal volume of the reservoir thus causing the bung to move distally and forcing the distal volume of primary medicament out of the reservoir and out of the distal injection needle. The distal diameter of the reservoir may be slightly larger than the proximal volume, and may be longer than the bung. Here, the bung may come to rest in a free space that will allow the primary and secondary medicament from the proximal volume to flow around the bung and out of the injection needle when the user next sets and injects a dose.

In another embodiment the reservoir in the medicated module could be a capsule or vial sealed at both ends with septa or other sealing means. The capsule could be positioned in the reservoir such that it is not in fluid communication with either of the two needle cannulae before a dose is delivered. For delivering a dose, a needle guard may be retracted and a guard lock may be in a first, unlocking, position. Preferably, hollow needle cannulae are mounted securely in the medicated module and are configured to pierce the septa located on the top and bottom ends of the capsule. Prior to piercing the capsule the needles may be only in fluid communication with the top and bottom of the reservoir to define a fluid flow path that bypasses the capsule. This fluid flow path or channel may be used in the priming function of the delivery device. This bypass could be achieved by a number of designs provided that the primary medicament could flow to the dispense interface without interacting with the medicament contained within the medicated module reservoir. More preferably the bypass is configured as a part of the reservoir or the capsule components to allow primary medicament to flow from the primary reservoir through the proximal needle cannula into the bypass and then out through the distal or injection needle. When the module is applied to an injection site, for example such that a needle guard is retracted, the two needle cannulae pierce the capsule septa and become fluidly engaged with the medicament in the capsule.

The disclosed medicated module can also have indicia indicating an injection status (or position of the guard lock). In particular, the indicia may be located on an outer sleeve surrounding the guard lock, and as an example a rotating sleeve of the guard lock. The indicia may be visible through a window, for example located in the outer sleeve. The indicia may show numbers, letters, colors, symbols, or combinations of these and may have a tactile or audible indicator.

The needle guard may reduce the risk of accidental needle sticks as well as reduce the anxiety of users suffering from needle phobia. The needle guard is preferably configured to move axially in both the distal and proximal directions when pressed against an injection site. When the module is removed or withdrawn from the patient, the guard is returned to a position covering the needle (this may or may not be the original starting position depending on the specific design of the guard) its original starting location. In a preferred configuration, the guard will be locked from further axial movement, preventing exposure of the distal needle cannula.

Locking of the guard after axial movement can be accomplished in many ways that are known to the art, such as, a moving or sliding lock contained within the module. However, a preferred method includes the use of a rotating sleeve. The moving lock design is one configured such that when the guard moves axially in the proximal direction it engages (picks up) the moving lock and then when the guard reverses direction (moving in the distal direction) it carries with it the moving lock. At a point when the guard has finished its reverse movement the moving lock becomes fixed or locked to a non-moving portion of the medicated module while remaining engaged to the guard. This prevents the guard from further axial movement in either direction.

The rotating sleeve type lock may be constrained from moving axially, but can rotate relative to the guard. As mentioned the rotating sleeve or guard lock may have four positions. A first position could be where the guard is unlocked to allow axial movement. Here, a reservoir in the module may be isolated so that a primary medicament contained in a separate reservoir can be used to prime an attached delivery device using, for example, a bypass around, or through, or independent of, the reservoir in the module. The rotating sleeve may move to a second position when the guard moves axially during application/pressing the module to an injection site (whether or not the dose button is actually activated). Then, the guard may be returned to its starting position (extended proximally) upon removal from the injection site. In this second position the rotating sleeve may lock the guard from further axial movement in a position where the guard completely covers the injection needle. The third position of the rotating sleeve may be triggered when the user activates the release mechanism, for example slides or pushes the button, to unlock the needle guard so as to allow a second use of the injection needle. The fourth position may be achieved when the guard is retracted for the second time and returned to its starting, extended position. In this last position the rotating sleeve may permanently lock the guard from further retraction such that unlocking by the release mechanism is disabled.

According to a specific embodiment, a medicated module attachable to a drug delivery device is disclosed, wherein the drug delivery device comprises a primary reservoir of medicament and wherein the medicated module comprises a second medicament. The medicated module further comprises a reservoir containing the second medicament, a needle guard to provide protection against at least one needle cannula arranged in a portion of the medicated module and configured to move in an axial direction during application to an injection site, a guard lock for at least temporarily disabling axial movement of the needle guard and a release mechanism operably connected to the guard lock for unlocking the guard lock such that axial movement of the needle guard is enabled.

According to a second specific embodiment a medicated module attachable to a drug delivery device is disclosed. The medicated module comprises a housing having a proximal end and a distal end, where the proximal end has a connector configured for attachment to a drug delivery device, a reservoir in a portion of the housing comprising a single dose of a medicament, a guard operably connected to the housing and configured to move in an axial direction during application to an injection site, a guard lock and a button operably connected to the guard lock.

According to a further aspect, a needle guard assembly for a drug delivery device is disclosed. The needle guard assembly comprises a needle guard, a guard lock and a release mechanism for the guard lock as described above. The needle guard assembly may comprise or may not comprise a medicament reservoir.

According to a further aspect, there is provided a medicated module attachable to a drug delivery device comprising a reservoir containing a movable bung dividing the reservoir into a distal volume and a proximal volume. The medicated module may further comprise any of the features as described above. As an example, the medicated module may comprise a needle guard, a guard lock and a release mechanism. In one embodiment, the medicated module may be free from a needle guard.

According to a further aspect, a drug delivery system to deliver two or more medicaments is disclosed. The drug delivery system may comprise a medicated module as described above and a primary reservoir of medicament containing at least one drug agent. The medicated module may be configured for fluid communication with the primary reservoir.

The drug delivery system may be operable through a single dose setter and a single dispense interface and may comprise a housing containing a single dose setter. The dose setter may be operably connected to a primary reservoir of medicament containing at least one drug agent and a dose button may be operably connected to the primary reservoir of medicament. The system may also have a single dispense interface configured for fluid communication with the primary reservoir and a medicated module. The medicated module may comprise a proximal end and a distal end, where the proximal end may have a connector configured for attachment to the housing of the drug delivery device. The module preferably has a sealed capsule containing a single dose of a second medicament, a needle guard configured to move in an axial direction when the module is applied to an injection site, and a release mechanism, for example a button, to release a guard lock to allow for a second injection using the same output needle. The drug delivery device may be configured such that with a single activation of the dose button medicament from the primary reservoir and the second medicament from the capsule can be expelled through the output needle.

Our disclosure also covers a method of dispensing a fixed dose of one medicament and a variable dose of a primary medicament from separate reservoirs. The method involves the steps of first attaching a medicated module to a delivery device, where the module may have a needle guard lock override feature to allow the user to consciously reuse the output needle to perform a further, for example a second, injection of primary medicament. Before the needle guard is retracted for the first time, the user may be enabled to prime the dose delivery device using only the primary medicament, without dispensing the second medicament. After priming, if the user has not already set a dose of the first medicament, the user then may set a dose of a first medicament contained in a primary reservoir of the drug delivery device using a single dose setter, and then inserts the needle into an injection site. When the user activates a dose button the set dose of the first medicament from the primary reservoir may be caused to move in a distal direction and simultaneously forces substantially all of a non-user set dose (e.g. a single dose) of a second medicament from a secondary reservoir contained in a medicated module through a single dispense interface, preferably a hollow injection needle. Upon completion of the delivery procedure, substantially all of the second medicament may have been expelled as well as the selected dose of the first medicament through the single dispense interface. By "substantially all" we mean that at least about 80% of the second medicament is expelled from the drug delivery device, preferably at least about 90% is expelled. Upon completion of the injection, the needle guard may prevent a second delivery or insertion through a locking mechanism as described previously, unless the user activates the guard lock override feature, for example the release mechanism as described above, to allow a second injection of only the primary medicament. The second injection may be the final injection. In particular, the needle guard may be permanently locked after the second injection.

The combination of compounds as discrete units or as a mixed unit may be delivered to the body via an integral needle. This would provide a combination drug injection system that, from a user's perspective, would be achieved in a manner that very closely matches the currently available injection devices that use standard needles.

The disclosed medicated module can be designed for use with any drug delivery device with an appropriate compatible interface. However, it may be preferable to design the module in such a way as to limit its use to one exclusive primary drug delivery device (or family of devices) through employment of dedicated or coded features to prevent attachment of a non-appropriate medicated module to a non-matching device. In some situations it may be beneficial to ensure that the medicated module is exclusive to one drug delivery device while also permitting the attachment of a standard drug dispense interface to the device. This would allow the user to deliver a combined therapy when the module is attached, but would also allow delivery of the primary compound independently through a standard drug dispense interface in situations, such as, but not limited to, dose splitting or top-up of the primary compound.

A particular benefit of the disclosed medicated module and drug delivery device may be that the medicated module makes it possible to tailor dose regimes when required, especially where a titration period is necessary for a particular drug. The medicated module could be supplied in a number of titration levels with obvious differentiation features such as, but not limited to, aesthetic design of features or graphics, numbering etc, so that a patient could be instructed to use the supplied medicated module in a specific order to facilitate titration. Alternatively, the prescribing physician may provide the patient with a number of "level one" titration medicated modules and then when these were finished, the physician could then prescribe the next level. A key advantage of this titration program is that the primary device remains constant throughout.

In a preferred embodiment, the primary drug delivery device is used more than once and therefore is multi-use, however, the drug delivery device may also be a single use disposable device. Such a device may or may not have a replaceable reservoir of the primary drug compound. It is also possible to have a suite of different medicated modules for various conditions that could be prescribed as one-off extra medication to patients already using a standard drug delivery device. Should the patient attempt to reuse a previously used medicated module, the medicated module may include the locking needle guard that is activated after drug dispense or insertion that could alert the patient to this situation. Only by consciously unlocking the module can the user perform a second injection with the same medicated module. Other means of alerting the user may include some (or all) of the following:

Physical prevention of medicated module re-attachment to the primary drug deliver device once the module has been used and removed.

Physical/hydraulic prevention of subsequent liquid flow through the drug dispense interface once it has been used.

Physical locking of the dose setter and/or dose button of the primary drug delivery device.

Visual warnings (e.g. change in color and/or warning text/indicia within an indication window on the module once insertion and/or fluid flow has occurred).

Tactile feedback (presence or absence of tactile features on the outer surface of the module hub following use).

A further feature of this embodiment may be that both medicaments are delivered via one injection needle and in one injection step. This offers a convenient benefit to the user in terms of reduced user steps compared to administering two separate injections. This convenience benefit may also result in improved compliance with the prescribed therapy, particularly for users who find injections unpleasant or who have cognitive or dexterity difficulties.

Our disclosure also covers a method of delivering two medicaments stored in separate primary packages. The medicaments may both be liquid, or alternatively one or more of the medicaments may be a powder, suspension or slurry. In one embodiment the medicated module could be filled with a powdered medicament that is either dissolved or entrained in the primary medicament as it is injected through the medicated module.

These as well as other advantages of various aspects of the present invention will become apparent to those of ordinary skill in the art by reading the following detailed description, with appropriate reference to the accompanying drawings.

The scope of the invention is defined by the content of the claims. The invention is not limited to specific embodiments but comprises any combination of elements of different embodiments. Moreover, the invention comprises any combination of claims and any combination of features disclosed by the claims.

BRIEF DESCRIPTION OF THE DRAWINGS

Exemplary embodiments are described herein with reference to the drawings, in which.

DETAILED DESCRIPTION

Figure 1:
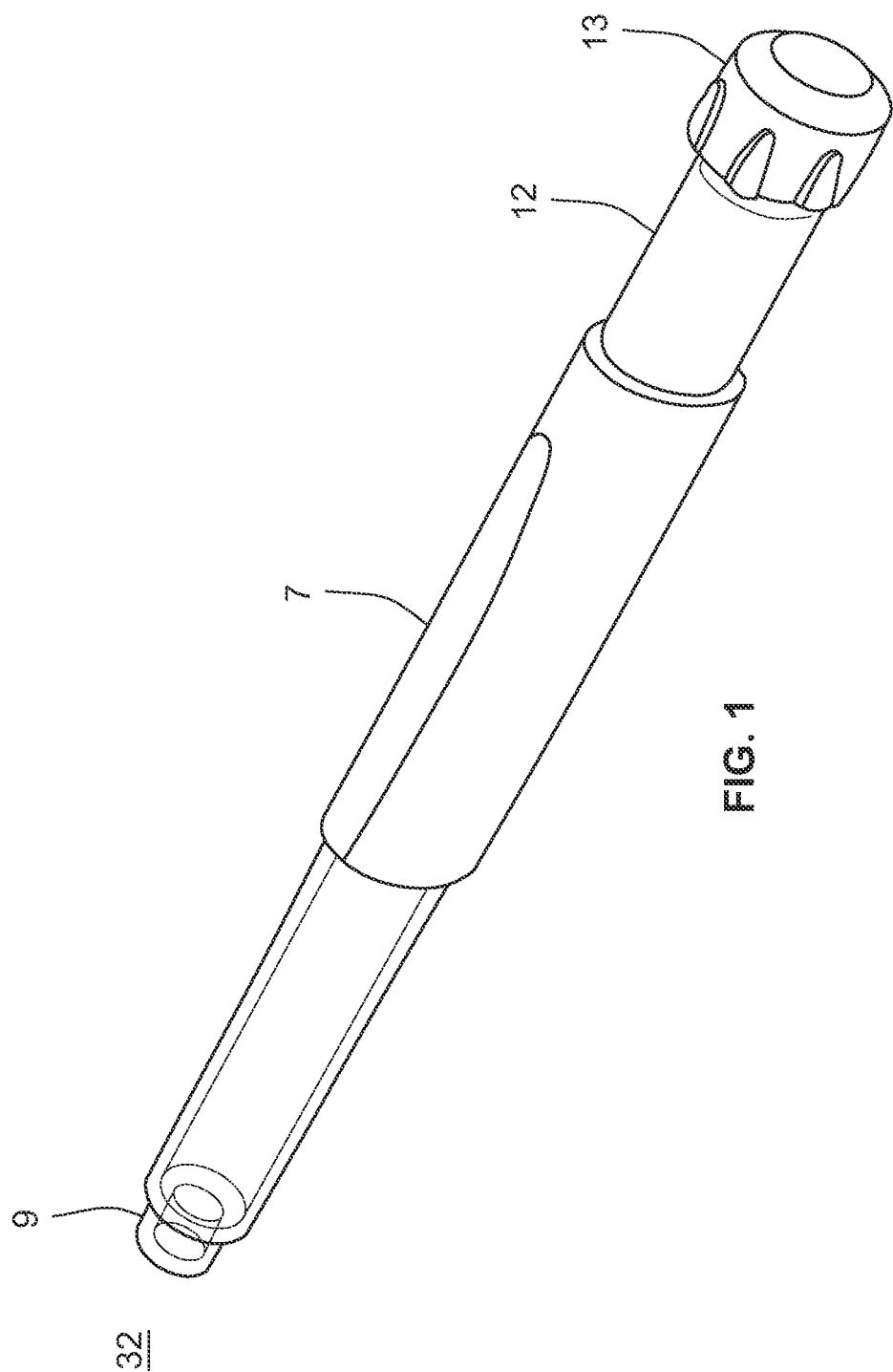
FIG. 1 illustrates one possible drug delivery device.

Specific embodiments of the disclosed medicated module and drug delivery system enable administering a fixed and predetermined dose of a secondary drug compound (medicament) and a variable dose of a primary or first drug compound through a single output or drug dispense interface. Setting the dose of the primary medicament by the user may automatically determine the fixed dose of the second medicament, which preferably is a single dose contained in a reservoir or sealed capsule. In a preferred embodiment the drug dispense interface is a needle cannula (hollow needle). FIG. 1 illustrates one example of a drug delivery device 7 to which a medicated module 4 (see FIGS. 2-5) can be attached to the connection means 9 of distal end 32. Each medicated module 4 is preferably self-contained and provided as a sealed and sterile disposable module that has an attachment means 8 compatible to the attachment means 9 at the distal end 32 of device 7. Although not shown, the medicated module could be supplied by a manufacturer contained in a protective and sterile container, where the user would peel or rip open a seal or the container itself to gain access to the sterile medicated module. In some instances it might be desirable to provide two or more seals for each end of the medicated module.

Any known attachment means 8 can be used to attach the medicated module 4 to the chosen drug delivery device 7, including all types of permanent and removable connection means, such as threads, snap locks, snap fits, luer locks, bayonet, snap rings, keyed slots, and combinations of such connections. FIGS. 2-5 illustrate the attachment means 8 as a snap fit that would engage a rib or possibly threads 9 on the distal end 32 of drug delivery device 7. The embodiments shown in FIGS. 2-5 have the benefit of the second medicament as a single dose being contained entirely within reservoir 31 or capsule 21. Use of a capsule 21 (FIGS. 4-5) minimizes the risk of material incompatibility between the second medicament and the materials used in the construction of the medicated module 4, specifically housing 10, inner housing 11 or any of the other parts used in the construction of the module 4 it also permits the capsule 21 to be manufactured as a separate assembly and then fed into the main assembly.

To minimize the residual volume of the second medicament, caused by recirculation and/or stagnant zones, that might remain in the reservoir 31 or capsule 21 at the end of the dispense operation, it is preferable to use a flow distribution system (not shown) to maximize the amount of the second medicament dispensed from the medicated module. When a capsule 21 is used, it comprises a vial that can be sealed with septa 6a and 6b (see FIG. 4), which are fixed to the capsule 21 using ferrules or any type of sealing means. Preferably, ferules made from a crimpable material, most preferably a metal, such as aluminum can be used. Regardless of whether the reservoir 31 alone or a capsule 21 within the reservoir 31 is used, preferably the design of the flow distribution system should ensure that at least about 80% of the second medicament is expelled from the reservoir 31 or capsule 21 through the distal end of needle 3. Most preferably at least about 90% should be expelled. Ideally displacement of the first or primary medicament from the primary reservoir 14 through the capsule 21 will displace the second medicament without substantial mixing of the two medicaments.

The medicated module 4 comprises two needle cannulae 3, 5. One needle cannula 3 is arranged at the distal end of the module 4. The other needle cannula 5 is arranged proximally from the first needle cannula 3. A reservoir 31 is axially arranged between the needle cannulae 3, 5. The needle cannulae 3, 5 are positioned to establish fluid communication with the reservoir 31.

Attachment of the medicated module 4 to the multi-use device 7 causes the engagement needle 5 located in the proximal end of module 4 to penetrate septum 1 sealing the distal end of the cartridge 14 of the multi-use device 7. Once the engagement needle 5 has passed through the septum 1 of the cartridge 14, fluid connection is made between the first or primary medicament and needle 5. At this point the system can be primed or the dose of the multi-use device 7 set using a dose setter 12 (see FIG. 1) in the normal manner (e.g. by dialing out the appropriate number of units or cocking the device if only a single dose is possible). Dispense of the medicaments is then achieved by subcutaneously injecting the medicaments via activation of a dose button 13 on device 7. In this regard, the dose button 13 can be any triggering mechanism that causes the dose of the first medicament that was set by the dose setter 12 to move towards the distal end 32 of the device 7. In a preferred embodiment the dose button 13 is operably connected to a spindle that engages a piston in the primary reservoir 14 of the first medicament.

Figure 3:
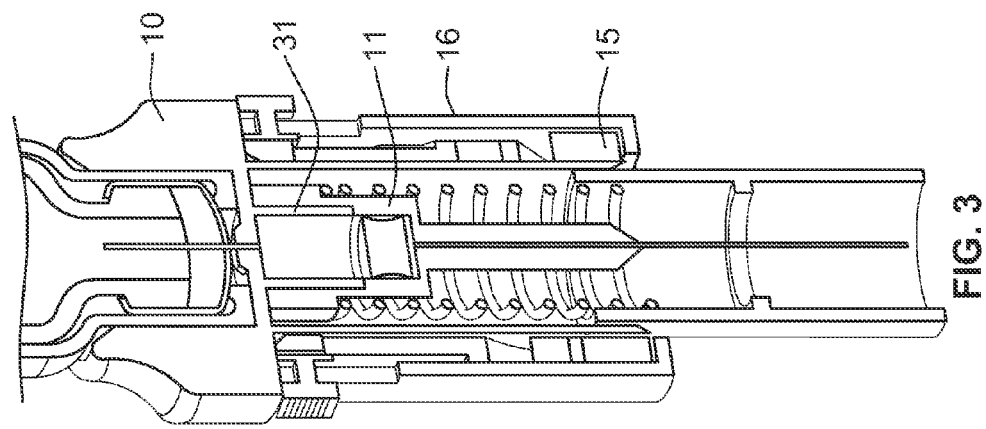
FIG. 3 illustrates a sectioned view of the embodiment of the medicated module shown in FIG. 2 after the module has been primed with primary medicament.
Figure 2:
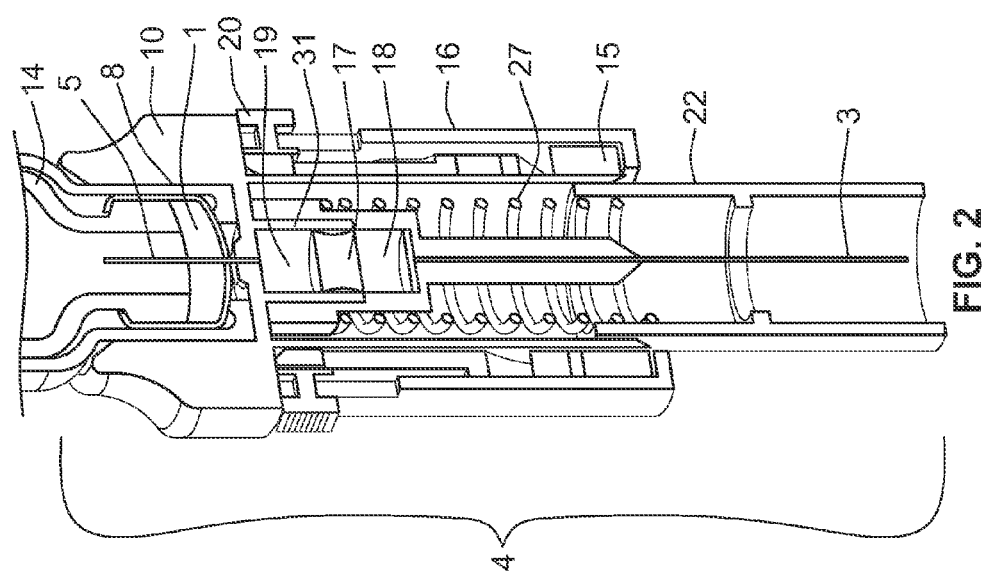
FIG. 2 illustrates a sectioned view of an embodiment of the medicated module having a reservoir containing a bung to separate the second medicament from a fixed volume of primary medicament.

One embodiment of the medicated module 4 is illustrated in FIGS. 2-3. In this embodiment the module 4 comprises a housing 10, an inner housing 11, an outer housing 16, and a rotating sleeve 15. A reservoir 31 is formed from a portion of the inner housing 11 and the housing 10 to define a distal volume 18 and a proximal volume 19, respectively. Bung 17, which provides a liquid seal between the single dose of second medicament occupying the proximal volume 19 and a fixed volume of primary medicament occupying the distal volume 18, separates these two volumes. The bung 17 is initially in a first position and in a sealed engagement with the interior walls of the proximal volume or upper portion of reservoir 31. In some cases this secondary medicament may be a mixture of two or more drug agents that can be the same or different from the primary drug compound in the drug delivery device 7.

The user primes the drug delivery system 7 by setting a dose of the primary medicament in cartridge 14 using dose setter 12 less than or equal in volume to the fixed volume of primary medicament in the distal volume of reservoir 31. Upon activation of dose button 13, the set dose of primary medicament flows from cartridge 14, through needle 5 and into proximal volume 19 creating a driving or pressure force on bung 17 that causes the bung 17 to move in a distal direction into distal volume 18. As bung 17 moves distally, the primary medicament in the distal volume 18 is forced out through needle 3 thus priming the system. The single dose of the secondary medicament is now mixed with the primary medicaments from the cartridge 14 inside the reservoir 31. At the end of the priming procedure the bung 17 will be in a second position in the distal volume of the reservoir 31 and no longer in a sealing engagement with the interior of the reservoir 31. This lack of a sealing engagement and resultant availability of flow channels will now allow the mix of the secondary and primary medicaments in the reservoir to be dispensed around the bung 17 and out the injection needle 3 upon subsequent dose setting and activation of the injection button 13. FIG. 3 shows the position of the bung after the priming step.

In an alternative embodiment, the reservoir 31 contains sealed capsule 21, which holds a fixed single dose of the secondary medicament. In some cases this secondary medicament may be a mixture of two or more drug agents that can be the same or different from the primary drug compound in the drug delivery device 7. Preferably the capsule 21 is permanently contained within the medicated module 4 and is designed to administer a fixed predetermined dose of a second medicament, however, in some cases it may be preferred to design the module 4 such that the capsule 21 can be removed when empty and replaced with a new capsule 21.

Figure 4:
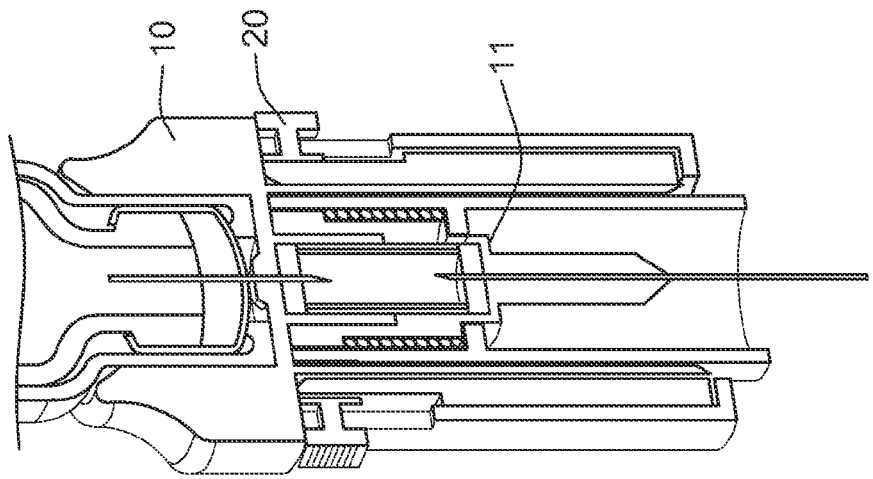
FIG. 4 illustrates a sectioned view of another embodiment of the medicated module having a reservoir containing a capsule containing the second medicament positioned in a bypass or priming mode.
Figure 5:
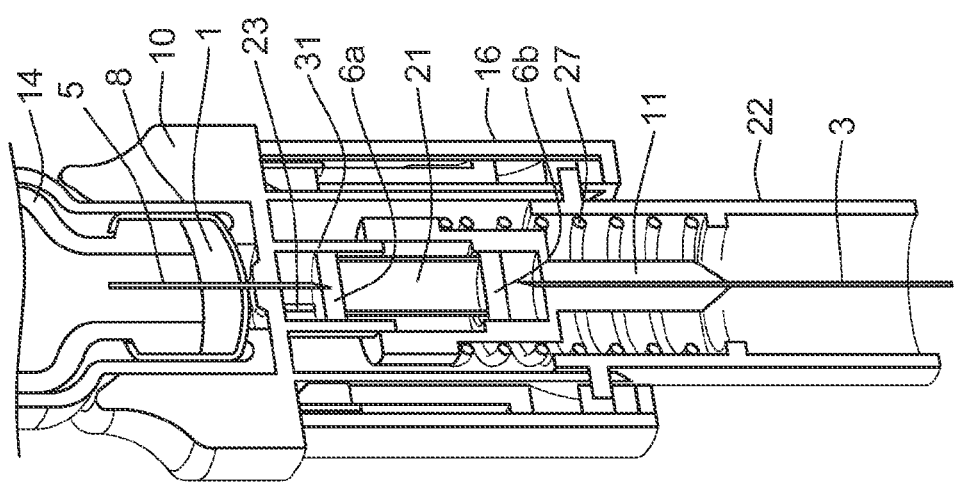
FIG. 5 illustrates a sectioned view of the embodiment of the medicated module shown in FIG. 4 when the needle guard is retracted causing the needles to engage the capsule.
Figure 6:
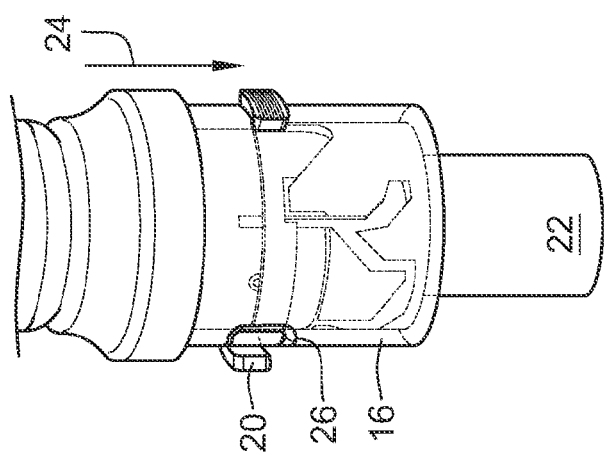
FIGS. 6-9 show the rotating sleeve/guard lock of the medicated module in different positions.

In the embodiments shown in FIGS. 4-5, capsule 21 has ends that are sealed with pierceable membranes or septa 6a and 6b that provide a hermetically sealed and sterile reservoir for the second medicament. A primary or engagement needle 5 can be fixed in the housing 10 of the module and configured to engage capsule 21 when guard 22 is retracted, such as when it is applied to an injection site. The output needle 3 is preferably mounted in inner housing 11 and initially protrudes above the lower (distal) surface of cavity 23. In this starting position as shown in FIG. 4, needles 3 and 5 are not in fluid communication with the medicament contained in capsule 21. One possible design to prevent the needles from initially piercing the capsule septa 6a, 6b would include support features, such as biasing spring, washer, or a bellow type structure that keep the capsule 21 suspended in the cavity to avoid penetration by needles 3 and 5 until required. In this non-collapsed or suspended state, a priming step can be performed where primary medicament from cartridge 14 can flow from needle 5 into cavity 23, around capsule 21, and out needle 3.

When the volume of the cavity 23 is decreased as the inner housing 11 is forced proximally by the needle guard 22 the capsule 21 is moved axially forcing both needles 3, 5 to pierce the septa 6a, 6b. If the support features were bellows, then the bellows would collapse as the guard 22 retracts and the inner housing 11 moves proximally. Alternatively, the capsule 21 can be configured to move or slide within the cavity 23 as it is pushed proximally by the inner housing 11. Flow around or bypassing capsule 21 is accomplished by configuring the capsule to have one or more vanes or channels down the outside of the capsule 21. Alternatively, the inner housing 11 or internal walls of the cavity 23 could have these vanes or fluid channels incorporated therein and then the outer walls of the vial could be smooth. Regardless of the specific design, the proximal end of needle 3 only pierces the lower membrane 6b when guard 22 is retracted causing inner housing 11 to move proximally. This movement of inner housing 11 eventually causes upper septa 6a to engage the distal end of needle 5. This retracted guard position is shown in FIG. 5.

Figure 8:
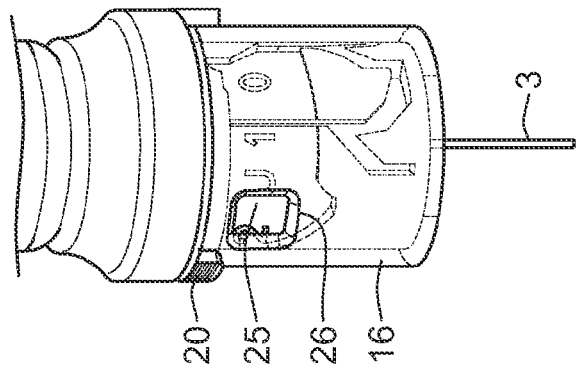
Figure 9:
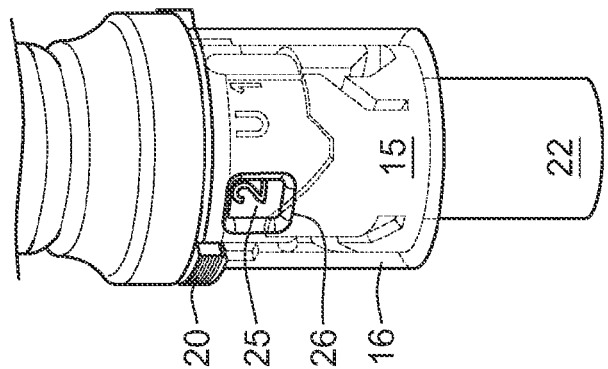

The guard or safety shield 22 could be any design that would prevent accidental needle sticks and/or reduce the anxiety experienced by users who suffer from needle phobia. The exact design of the safety shield is not critical to the present disclosure, however, a preferred design, as disclosed below, is one that allows only a single use of needle 3, unless the user consciously activates button 20 to unlock the guard 22 for a second injection. Button 20 is operably connected to rotating sleeve 15 such that when the user pushes button 20 in a distal or downward direction 24 (see FIG. 9), the rotating sleeve 15 is moved to a third position where the guard 22 is unlocked. Guard 22 is operably connected to the rotating sleeve 15 such that the guard 22 is locked from axial movement when the rotating sleeve 15 is in either a second (FIG. 8) or fourth position. During dose delivery guard 22 moves or slides proximally relative to outer housing 16 and is constrained rotationally. This proximal movement of the guard 22 activates or loads a resilient or biasing member within the module housing, which preferably could be a compression spring 27 or a set of one or more flexible arms. This biasing member may be configured to create a force on inner housing 11 to cause it move proximally.

Figure 7:
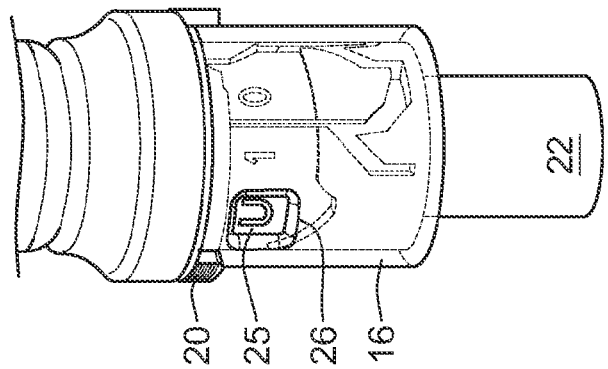

Preferably, the connection between the guard 22 and the rotating sleeve 15 is a pin/groove combination as illustrated in FIGS. 6-9. This pin/groove combination can be configured such that the rotating sleeve 15 has two positions where the guard 22 can move axially and two positions where the rotating member 15 blocks or locks the guard 22 from axial movement. Preferably, the needle guard 22 is locked from axial movement after the first retraction of the guard 22 (FIG. 7). Only a conscious movement of button 20 (FIG. 9) in direction 24 will rotate the rotating member 15 to the third position where the guard 22 is unlocked for one additional retraction. The second refraction of the guard 22 (i.e. during injection) followed by extension back to the starting position will move the rotating member 15 to fourth and final position that will preferably permanently lock the guard 22 from axial movement. In this final locked position the guard 22 will completely cover the injection needle 3 for safe handling and disposal. As shown in FIGS. 6-9, rotating sleeve 15 can contain indicia, such as letters or numerals 25 or any combination of letters or numerals or colors or images, to indicate the position of the guard lock and/or the number of injections remaining. This indicia is visible through a window 26 in the outer housing 16.

In any of the above described embodiments the second medicament may be either in a powdered solid state, any fluid state contained within the secondary reservoir or microcapsule, or coated to the inside surface of the drug dispense interface. The greater concentration of the solid form of the medicament has the benefit of occupying a smaller volume than the liquid having lower concentration. This in turn reduces the ullage of the medicated module. An additional benefit is that the solid form of the second medicament is potentially more straightforward to seal in the secondary reservoir than a liquid form of the medicament. The device would be used in the same manner as the preferred embodiment with the second medicament being dissolved by the first medicament during dispense.

To minimize diffusion of the secondary medicament contained in the reservoir capsule within the medicated module into the primary medicament during dispense of the medicaments a flow distribution system may be used. Such a system also ensures efficient expulsion of the second medicament from the system and greatly minimizes residual volume. One possible embodiment of a flow distribution system would be a flow distributor configured as an annular pin that is positioned in capsule 21 and configured such that the secondary medicament fills flow channels that are defined by the shape and location of one or more support ribs. The flow distributor (annular pin) can be constructed of any material that is compatible to the primary and secondary medicaments. A preferred material would be that typically used to manufacture septa or pistons (bungs) found in multi-dose medicament cartridges, although any material that is compatible with the medicament during long term storage would be equally applicable. The shape of the flow channels can be optimized for a plug flow of medicament by varying the dimensions and number of support ribs. The cross-sectional area of the annulus formed between the flow distributor and the wall of the vial should be kept relatively small. The volume available to store the secondary medicament would equal the internal volume of the capsule minus the volume of the flow distributor. Therefore if the volume of the flow distributor is marginally smaller than the internal volume of the capsule, a small volume is left which the secondary medicament occupies. Hence the scale of both the capsule and the flow distributor can be large while storing a small volume of medicament. A further benefit of this is that as the available volume for medicament is defined by the difference in volumes between the flow distributor and its housing, the external capsule geometry is not dictated by the volume of medicament. Resultantly for small volumes of secondary medicament (e.g. 50 micro liters) the capsule can be of an acceptable size for handling, transport, manufacture, filling and assembly.

The connection or attachment between the drug delivery device and the medicated module of the above described embodiments may contain additional features (not shown), such as connectors, stops, splines, ribs, grooves, and the like design features, that ensure that specific medicated modules are attachable only to matching drug delivery devices. Such additional features would prevent the insertion of a non-appropriate medicated module to a non-matching injection device and may prevent the use of a standard injection means/interface with the devices.

The shape of the medicated module may be a cylindrical body or any other geometric shape suitable for defining a fluid reservoir or for containing discrete self-contained reservoir of the secondary medicament and for attaching one or more needle cannula. The reservoir can be manufactured from glass or other drug contact suitable material. The integrated injection needle can be any needle cannula suitable for subcutaneous or intramuscular injection.

Preferably, the medicated module is provided by a drug manufacturer as a stand-alone and separate device that is sealed to preserve sterility. The sterile seal of the module is preferably designed to be opened automatically, e.g. by cutting, tearing or peeling, when the medicated module is advanced or attached to the drug delivery device by the user. Features such as angled surfaces on the end of the injection device or features inside the module may assist this opening of the seal.

The medicated module should be designed to operate in conjunction with a multiple use injection device, preferably a pen-type multi-dose injection device, similar to that illustrated in FIG. 1. The injection device could be a reusable or disposable device. By disposable device it is meant an injection device that is obtained from the manufacturer preloaded with medicament and cannot be reloaded with new medicament after the initial medicament is exhausted. The device may be a fixed dose or a settable dose and preferably a multi-dose device, however, in some cases it may be beneficial to use a single dose, disposable device.

A typical injection device contains a cartridge or other reservoir of medication. This cartridge is typically cylindrical in shape and is usually manufactured in glass. The cartridge is sealed at one end with a rubber bung and at the other end by a rubber septum. The cartridge is introduced in the device before the medicated module 4 is attached to the device. The cartridge of the device is, at least partly, filled with first medicament before it is attached to the device. The injection device is designed to deliver multiple injections. The injection device further comprises a dose setter; the dose setter may be operably connected to the reservoir. The injection device comprises a dose button; the dose button may be operably connected to the reservoir. The dose button may be any triggering mechanism that causes the dose of the medicament that was set by the dose setter to move distally towards the distal end of the device. In a preferred embodiment, the dose button is operably connected to a spindle that engages a piston in the reservoir. In a further embodiment the spindle is a rotatable piston rod comprising two distinct threads. The delivery mechanism is typically powered by a manual action of the user, however, the injection mechanism may also be powered by other means such as a spring, compressed gas or electrical energy.

Exemplary embodiments of the present invention have been described. Those skilled in the art will understand, however, that changes and modifications may be made to these embodiments without departing from the true scope and spirit of the present invention, which is defined by the claims.

We claim:

1. A medicated module attachable to a drug delivery device, wherein the drug delivery device comprises a primary reservoir of medicament and a distal end with first attachment means, wherein the medicated module comprises a second medicament, the medicated module having a proximal end and a distal end and further comprising:
    a. second attachment means at the proximal end for attachment to the first attachment means of the drug delivery device;
    b. a second reservoir containing the second medicament;
    c. a cavity containing the second reservoir and a proximal needle cannula configured to provide fluid communication with the primary reservoir when the medicated module is connected thereto and a distal injection needle cannula, the second reservoir being arranged in the axial direction between the proximal and the distal needle cannula, and the proximal and distal needle cannula being configured to allow fluid communication with the second reservoir,
    d. a needle guard to provide protection against the injection needle cannula arranged in a portion of the medicated module and configured to move in an axial direction during application to an injection site;
    e. a guard lock for at least temporarily disabling axial movement of the needle guard; and
    f. a release mechanism operably connected to the guard lock for unlocking the guard lock such that axial movement of the needle guard is enabled.

2. The medicated module of claim 1, where the release mechanism comprises a button accessible to a user to move the button to unlock the guard lock to enable axial movement of the needle guard.

3. The medicated module of claim 1, where the guard lock comprises a rotating sleeve operably connected to the needle guard.

4. The medicated module of claim 1, wherein when the needle guard is removed or withdrawn from the patient it is configured to return to a position covering the injection needle, wherein the guard lock is configured to lock the needle guard from further axial movement when the needle guard has returned to the position covering the injection needle.

5. The medicated module of claim 1, where the activation of the release mechanism unlocks the guard lock to allow one or more additional retractions of the needle guard after dispensing the medicament and where after each retraction the guard lock at least temporarily locks the needle guard from axial movement.

6. The medicated module of claim 1, configured such that after a predefined number of retractions of the needle guard the needle guard is permanently locked from axial movement such that unlocking is disabled.

7. The medicated module of claim 1, where the second reservoir contains a movable bung dividing the second reservoir into a distal volume and a proximal volume.

8. The medicated module of claim 7, where the bung separates a single dose of secondary medicament in the proximal volume from a fixed amount of primary medicament in the distal volume.

9. The medicated module of claim 7 configured such that when the medicament from the primary reservoir flows into the proximal volume the bung is caused to move into the distal volume, thereby expelling medicament from the distal volume, and configured such that the medicament in the proximal volume is dispensable around the bung when the bung is in the distal volume position.

10. The medicated module of any of claim 1, comprising indicia for indicating an injection status of the drug delivery device.

11. The medicated module according to claim 1, where a fluid path is defined in the cavity bypassing the second reservoir.

12. The medicated module according to claim 1, where the second reservoir is a capsule sealed with top and bottom septa and where the capsule is positioned such that it is not in fluid communication with the distal and proximal needle cannula prior to retraction of the needle guard.

13. The medicated module of claim 1, where the second reservoir contains a liquid medicament.

14. A drug delivery system to deliver two or more medicaments comprising a medicated module according to claim 1 and further comprising:
- a primary reservoir of medicament containing at least one drug agent; where
- the medicated module is configured for fluid communication with the primary reservoir.

* * * * *